United States Patent
Wang et al.

(10) Patent No.: US 11,584,019 B2
(45) Date of Patent: Feb. 21, 2023

(54) SUBSTRATE CARRIER DETERIORATION DETECTION AND REPAIR

(71) Applicant: Taiwan Semiconductor Manufacturing Co., Ltd., Hsinchu (TW)

(72) Inventors: Jen-Ti Wang, Taichung (TW); Chih-Wei Lin, Hsinchu (TW); Fu-Hsien Li, Taichung (TW); Yi-Ming Chen, Taipei County (TW); Cheng-Ho Hung, Tainan (TW)

(73) Assignee: TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 34 days.

(21) Appl. No.: 17/114,178

(22) Filed: Dec. 7, 2020

(65) Prior Publication Data
US 2021/0118665 A1  Apr. 22, 2021

Related U.S. Application Data

(62) Division of application No. 15/794,352, filed on Oct. 26, 2017, now Pat. No. 10,861,692.

(51) Int. Cl.
*B25J 11/00* (2006.01)
*G01B 11/30* (2006.01)
(Continued)

(52) U.S. Cl.
CPC ............ *B25J 11/008* (2013.01); *G01B 11/306* (2013.01); *H01L 21/67005* (2013.01);
(Continued)

(58) Field of Classification Search
CPC ..... B25J 11/005; B25J 11/008; G01B 11/306; H01L 21/67005; H01L 21/67389; H01L 21/67393
See application file for complete search history.

(56) References Cited

U.S. PATENT DOCUMENTS

| 5,373,737 A | 12/1994 | Hwang et al. |
| 6,779,760 B2 | 8/2004 | Chang et al. |

(Continued)

FOREIGN PATENT DOCUMENTS

| CN | 203466172 | 3/2014 |
| EP | 1343202 | 9/2003 |

(Continued)

OTHER PUBLICATIONS

Korean Intellectual Property Office, Notice of Allowance, dated Oct. 30, 2019, Application No. 10-2017-0158824.

*Primary Examiner* — James Keenan
(74) *Attorney, Agent, or Firm* — Haynes and Boone, LLP

(57) ABSTRACT

An apparatus for semiconductor manufacturing includes an input port to receive a carrier, wherein the carrier includes a carrier body, a housing installed onto the carrier body, and a filter installed between the carrier body and the housing. The apparatus further includes a first robotic arm to uninstall the housing from the carrier and to reinstall the housing into the carrier; one or more second robotic arms to remove the filter from the carrier and to install a new filter into the carrier; and an output port to release the carrier to production.

20 Claims, 7 Drawing Sheets

(51) Int. Cl.
  *H01L 21/67* (2006.01)
  *H01L 21/02* (2006.01)
  *H01L 21/66* (2006.01)
  *B25J 18/00* (2006.01)
  *G01B 11/24* (2006.01)
  *G01N 33/00* (2006.01)
  *H01L 21/673* (2006.01)
  *H01L 21/677* (2006.01)
  *B23P 6/00* (2006.01)
  *B25J 1/04* (2006.01)

(52) U.S. Cl.
  CPC . *B23P 6/00* (2013.01); *B25J 1/04* (2013.01); *B25J 11/005* (2013.01); *B25J 18/00* (2013.01); *G01B 11/24* (2013.01); *G01N 33/0004* (2013.01); *G01N 33/0013* (2013.01); *G01N 33/0024* (2013.01); *G01N 33/0029* (2013.01); *G01N 33/0031* (2013.01); *G01N 33/0062* (2013.01); *G01N 33/0063* (2013.01); *G01N 33/0065* (2013.01); *G01N 2033/0095* (2013.01); *H01L 21/0201* (2013.01); *H01L 21/02043* (2013.01); *H01L 21/02049* (2013.01); *H01L 21/673* (2013.01); *H01L 21/6779* (2013.01); *H01L 21/67389* (2013.01); *H01L 21/67393* (2013.01); *H01L 21/67733* (2013.01); *H01L 21/67736* (2013.01); *H01L 21/67742* (2013.01); *H01L 21/67775* (2013.01); *H01L 21/67778* (2013.01); *H01L 22/30* (2013.01); *Y10T 29/49769* (2015.01); *Y10T 29/49771* (2015.01)

(56) References Cited

U.S. PATENT DOCUMENTS

| | | | |
|---|---|---|---|
| 7,212,937 | B2 | 5/2007 | Friberg et al. |
| 7,400,383 | B2 * | 7/2008 | Halbmaier ........ H01L 21/67359 55/318 |
| 8,591,809 | B2 | 11/2013 | Ra et al. |
| 8,616,821 | B2 | 12/2013 | Ku et al. |
| 8,827,695 | B2 | 9/2014 | Hsiao et al. |
| 9,677,985 | B2 * | 6/2017 | Tsai ..................... G01N 15/06 |
| 9,881,820 | B2 * | 1/2018 | Wong ............... H01L 21/67383 |
| 10,818,530 | B1 * | 10/2020 | Atamny ............. H01L 21/6732 |
| 2005/0079041 | A1 | 4/2005 | Campbell et al. |
| 2010/0051502 | A1 * | 3/2010 | Cybulski ........... H01L 21/67389 220/756 |
| 2011/0278676 | A1 | 11/2011 | Cheng et al. |
| 2012/0083918 | A1 | 4/2012 | Yamazaki et al. |
| 2014/0200702 | A1 | 7/2014 | Liu et al. |
| 2015/0243667 | A1 | 8/2015 | Liaw |
| 2015/0303041 | A1 | 10/2015 | Lindenberg et al. |

FOREIGN PATENT DOCUMENTS

| | | |
|---|---|---|
| JP | 2009115655 | 5/2009 |
| JP | 2009523314 | 6/2009 |
| JP | 2014503989 | 2/2014 |
| KR | 20040002969 | 1/2004 |
| KR | 20130062942 | 6/2013 |
| KR | 20130125289 | 11/2013 |
| TW | 201618864 | 6/2016 |
| WO | 2017174540 | 10/2017 |

* cited by examiner

SUBSTRATE CARRIER DETERIORATION DETECTION AND REPAIR

PRIORITY

This is a divisional of U.S. patent application Ser. No. 15/794,352 filed Oct. 26, 2017, herein incorporated by reference.

BACKGROUND

In semiconductor fabrication, a wafer undergoes many processing steps in order to produce integrated circuits ("IC") thereon. These processing steps are performed by various different processing tools. When transferred among the processing tools, one or more wafers are carried inside a wafer carrier to protect the wafers from outside contamination. In addition, the wafer carrier (with the wafers inside) is purged with an inert gas to remove any chemical residues on the wafers. Otherwise, the chemical residues could adversely affect the subsequent processing.

The wafer carriers usually have one or more air filters. These air filters may become deteriorated (e.g., torn or clogged) after the wafer carrier is purged repeatedly. If the deteriorated air filter is not replaced timely, the wafer carrier will not be purged effectively, leading to wafer contamination and manufacturing defects.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
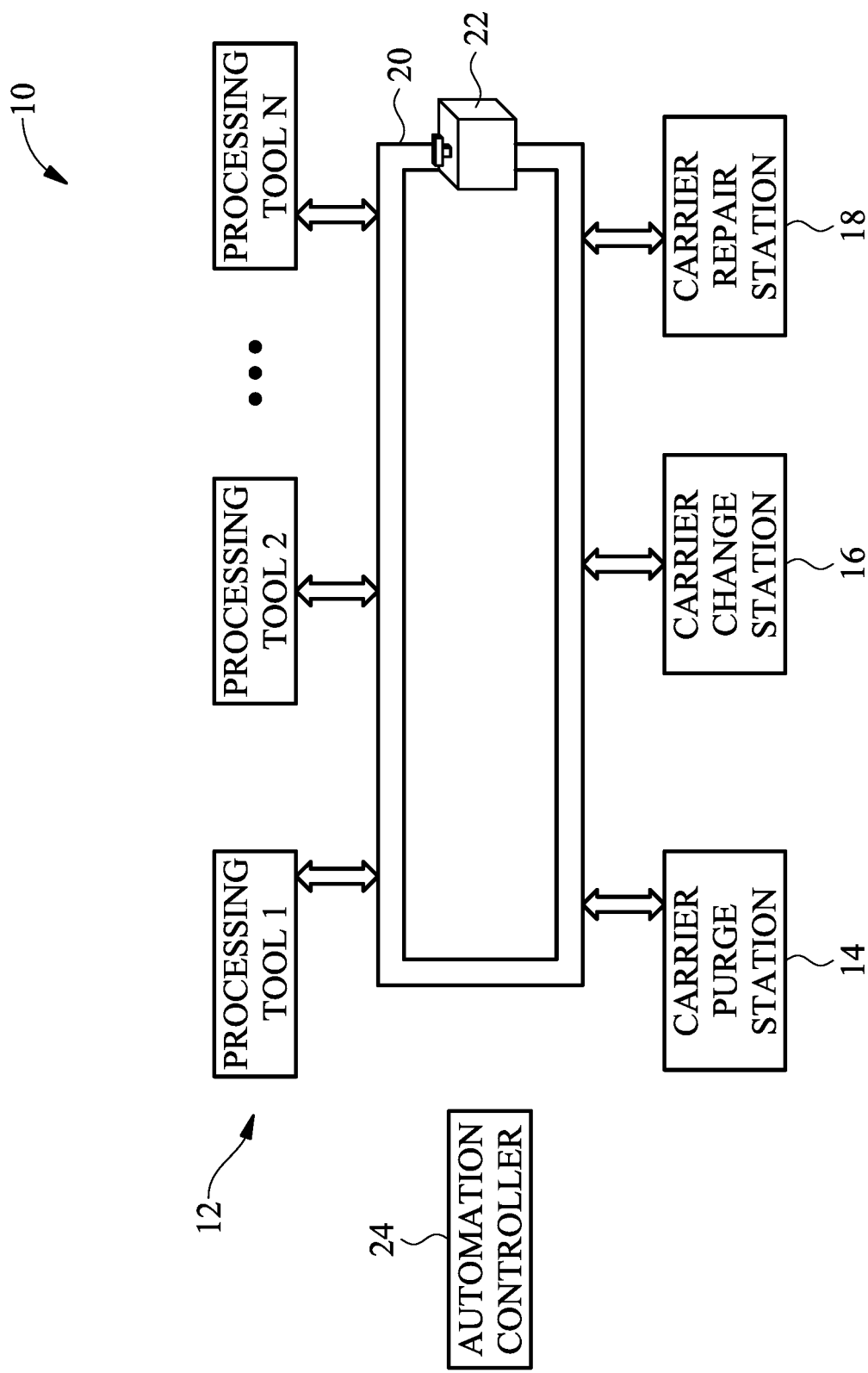
FIG. 1 illustrates a schematic view of a portion of a system for semiconductor fabrication, according to various aspects of the present disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

The present disclosure is generally related to semiconductor fabrication, more particularly to systems and methods for handling substrate carriers, such as wafer carriers, during semiconductor fabrication. An object of the present disclosure is to automatically detect deterioration in a substrate carrier, automatically replace the deteriorated substrate carrier with a new substrate carrier, and automatically repair the deteriorated substrate carrier. The present disclosure provides many benefits to semiconductor fabrication. First, it increases production efficiency and reduces production costs (e.g., it requires less labor and less manual work). Second, it is more reliable and reduces operational errors. Third, it detects substrate carrier deterioration timely and reduces wafer defects. As used herein, a substrate may be a wafer (such as a silicon wafer having a diameter of 125 mm, 150 mm, 200 mm, 300 mm, or 450 mm), a semiconductor substrate or wafer, a mask, a reticle, a plasma filtering plate, an adsorptive pad, any base material on which processing is conducted to produce new film or layers of material, and/or combinations thereof.

FIG. 1 illustrates a schematic view of a portion of a semiconductor fabrication system 10, constructed according to aspects the present disclosure. Referring to FIG. 1, the system 10 includes a plurality of semiconductor processing tools 12 including "Processing Tool 1," "Processing Tool 2," ... "Processing Tool N." The system 10 further includes one or more substrate carrier purge stations 14, one or more substrate carrier change stations 16, and one or more substrate carrier repair stations 18. The system 10 further includes an overhead hoist transport (OHT) 20, like a highway passing along the various tools and stations, for transporting one or more substrate carriers 22. The system 10 further includes an automation controller 24, such as an automated material handling system (AMHS), for dispatching the substrate carriers 22 among the tools and stations. In various embodiments, the system 10 may include other components, although not shown herein, or may omit some of the components discussed herein.

Each of the processing tools 12 may perform one or more tasks in association with manufacturing integrated circuits on substrates such as semiconductor wafers. The tasks may include front end of line (FEOL) processing, middle end of line (MEOL) processing, and back end of line (BEOL) processing. For example, the tasks may include substrate cleaning; material deposition such as epitaxy, chemical vapor deposition (CVD), physical vapor deposition (PVD), atomic layer deposition (ALD), and metal plating; etching such as dry etching, wet etching, reactive ion etching, and atomic layer etching (ALE); chemical mechanical planarization (CMP); baking; photoresist coating, exposing, developing, and ashing; and various other tasks. A processing tool 12 may process one substrate at a time or multiple substrates as a batch. In an embodiment, the processing tool 12 may include input and output loading docks that act as buffers for collecting a plurality of substrates before and after the processing.

A substrate or a plurality of substrates is moved from one processing tool to another processing tool according to a fabrication flow. Typically, after a processing step, a substrate is removed from a process tool that performed the processing step and transferred to a substrate carrier 22 where the substrate is temporarily stored until subsequent processing. The substrate carrier 22 provides a protective enclosure for housing therein one or more substrates, such as 1, 12, 13, or 25 substrates. In some embodiments, the substrate carrier 22 is a front opening unit pod (FOUP). FIG. 1 illustrates one substrate carrier 22 as part of the system 10. In various embodiments, the system 10 may include many substrate carriers 22 and the substrate carriers may be of different types. For example, substrate carriers for FEOL processing may be different from substrate carriers for BEOL processing. For example, the former may provide cleaner environment for substrates housed therein than the latter.

Still referring to FIG. 1, the carrier purge station 14 is configured to purge the substrate carrier 22 with an inert gas to ensure that the substrate carrier 22 continues to provide a clean and secure environment for substrates housed therein. A typical semiconductor fabrication flow may include many (e.g., about 70 to 100) purge steps. For example, the substrate carrier 22 may be purged after each of the following processes including dry etching, wet etching, ashing, dry cleaning, wet cleaning, deposition, CMP, plating, and other processes. For example, after gathering a certain number of substrates processed by a processing tool 12, the substrate carrier 22 may be transported (via the OHT 20) to the carrier purge station 14. Then, the carrier purge station 14 purges the substrate carrier 22 with an inert gas such as nitrogen or extra cleaning dry air. The purging removes chemical residues (e.g., $NH_3$, $SO_4$, F, Cl, $NO_3$, $PO_4$, etc.) from the substrate carrier 22. Thereafter, the substrate carrier 22 is transported (via the OHT 20) to the next processing tool 12 for further processing. In some steps of a fabrication flow, the substrate carrier 22 may be transported (via the OHT 20) from one processing tool 12 to another process tool 12 without being purged by the carrier purge station 14.

In the present embodiment, the substrate carrier 22 includes one or more air filters that help ensure a clean enclosure. After repeated purging, these air filters may become deteriorated (e.g., torn or clogged). The carrier purge station 14 is configured to detect the deterioration in these air filters, more details of which will be discussed in conjunction with FIG. 2. When the carrier purge station 14 detects that the air filters (and other parts coupled to the air filters) are no longer safe for the substrate carrier 22, it may indicate that to the automation controller 24, which may subsequently dispatch the substrate carrier 22 to the carrier change station 16 via the OHT 20. The carrier purge station 14 may communicate with the automation controller 24 through wireless or wired communication channel(s).

The carrier change station 16 is configured to replace a deteriorated substrate carrier with a new substrate carrier. For example, it is operable to move all substrates housed in the deteriorated substrate carrier into the new substrate carrier. It may also purge the new substrate carrier with an inert gas before releasing it to production (i.e., dispatching it to the processing tools 12). Alternatively, it may dispatch the new substrate carrier back to the carrier purge station 14, which purges the new substrate carrier. In some embodiments of the system 10, the carrier purge station 14 and the carrier change station 16 may be implemented as one piece of equipment or as separate pieces of equipment.

Deteriorated substrate carriers are dispatched (e.g., from either the carrier purge station 14 or the carrier change station 16) to the carrier repair station 18 via the OHT 20. In an embodiment, the carrier repair station 18 is configured to receive the deteriorated substrate carrier, open one or more screws, covers, and/or housings that cover air filters in the substrate carrier, remove the air filters, install new air filters, inspect the newly installed air filters, reinstall the screws, covers, and/or housings, and release the substrate carrier back to production. More details of the systems and methods for implementing the carrier repair station 18 will be further described in conjunction with FIGS. 3 and 4.

The system 10 provides many advantages over existing semiconductor fabrication systems. For example, the carrier purge station 14 enables automatic detection of deterioration in a substrate carrier. Such automatic detection increases production efficiency and reduces operational errors compared to visually inspecting the substrate carrier by an operator. For another example, the carrier repair station 18 enables automatic part-replacement in a substrate carrier, which also increases production efficiency and reduces operational errors compared to manually replacing the parts by an operator.

Figure 2:
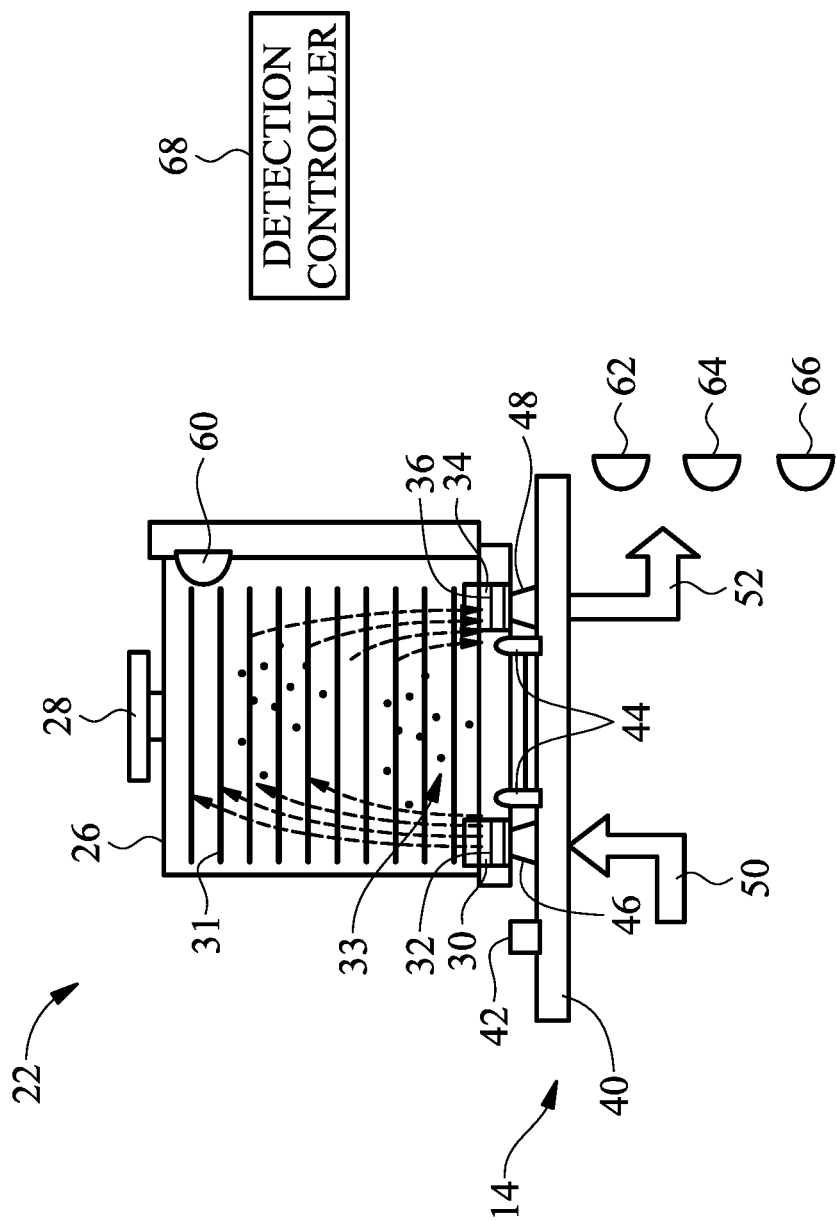
FIG. 2 illustrates a schematic view of a substrate carrier purge station, according to various aspects of the present disclosure.

Referring to FIG. 2, illustrated therein is the carrier purge station 14 purging a substrate carrier 22, in accordance with some embodiments. In the present embodiment, the substrate carrier 22 includes a body (or an outer cover) 26 and grooves or other structures inside the body 26 for securing a plurality of substrates (e.g., silicon wafers) 31 therein. The substrate carrier 22 further includes a handle 28 for attaching it to the OHT 20. The substrate carrier 22 further includes a door (not shown), through which the substrate 31 are placed into or taken out of the substrate carrier 22. The substrate carrier 22 includes an inlet 30 having an inlet air filter 32 installed therein, and an outlet 34 having an outlet air filter 36 installed therein. Within the inlet 30 and the outlet 34, the substrate carrier 22 may further include a filter housing (not shown) for securing the air filter, a cover (not shown) for fixing the filter housing, and optionally an O-ring (not shown) between the filter housing and the respective air filter. In some embodiments, the substrate carrier 22 may include more than one inlet and more than one outlet. In an embodiment, the substrate carrier 22 may further include a sensor 60 inside the housing 26. The sensor 60 may be a humidity sensor or an air pressure sensor.

Still referring to FIG. 2, in the present embodiment, the carrier purge station 14 includes a stage or base 40, an alignment sensor 42 for aiding the alignment of the carrier purge station 14 with the OHT 20, guide pins 44 for aligning the carrier purge station 14 with the substrate carrier 22 (e.g., by fitting into guide holes in the substrate carrier 22), an inlet 46 for supplying purge gas 50 into the inlet 30 of the substrate carrier 22, and an outlet 48 for extracting exhaust gas 52 out of the outlet 34 of the substrate carrier 22. The purge gas 50 may include nitrogen gas, extra clean dry air, or other suitable inert gas(es). As illustrated in FIG. 2, the purge gas 50 drives some chemical residues or particles 33 out of the substrate carrier 22 and into the exhaust gas 52. Some chemical residues or particles 33 may be adsorbed by the outlet air filter 36.

As discussed above, the same substrate carrier 22 may undergo numerous purging operations. After repeated use, the air filter 32 and/or the air filter 36 may deteriorate. For example, deposition of particles thereon may clog the air filters 32 and 36, thereby increasing its flow resistance and reducing its filtration quality. For another example, the air filters 32 and 36 may lose its mechanical strength and may become torn over time. Once the air filters 32 and 36 are torn, the substrate carrier 22 will lose its effectiveness in protecting the substrates 31 against the ambient. Therefore, detecting such deterioration (e.g., clogging or torn) timely is important for ensuring quality production.

In the present embodiment, the carrier purge station 14 further includes one or more humidity sensors 62, one or more gas flow rate sensors 64, and one or more particle sensors 66. The humidity sensor 62, the gas flow rate sensor 64, and the particle sensor 66 are installed near the outlet 48 in the present embodiment. Further, the sensors 62, 64, and 66 have direct contact with the exhaust gas 52 during the purging. The humidity sensor 62 is operable to detect the humidity of the exhaust gas 52. The gas flow rate sensor 64 is operable to detect the flow rate of the exhaust gas 52. The carrier purge station 14 may further include another gas flow rate sensor (not shown) that is operable to detect the flow rate of the purge gas 50. The particle sensor 66 is operable to detect the sizes of the particles in the exhaust gas 52 in an embodiment. Alternatively or additionally, the particle sensor 66 is operable to detect the number of particles (or the particle count) in the exhaust gas 52 or is operable to detect the density of particles in the exhaust gas 52. In various embodiments, the carrier purge station 14 may include one particle sensor 66 for detecting particle sizes, particle count, and particle density in the exhaust gas 52, or it may include separate particle sensors for performing the above functions respectively. Using the various sensors 60, 62, 64, and 66, the carrier purge station 14 is able to generate a health indicator of the substrate carrier 22. In an embodiment, the health indicator indicates whether or not the air filters 32 and 36 need to be replaced.

The carrier purge station 14 further includes a detection controller 68. In the present embodiment, the detection controller 68 is a computerized tool such as a computer with a software running thereon. For example, the detection controller 68 may include a processor or a microprocessor, an input device, a memory device, and a communication device interconnected by one or more buses; and may execute software instructions for performing various tasks of the carrier purge station 14. Some of these tasks are discussed below.

In an embodiment, the carrier purge station 14 generates the health indicator based on a measurement of air pressure inside the substrate carrier 22. For example, the detection controller 68 may read the air pressure value measured by the sensor 60, for example, using a wired or wireless connection between the two. For another example, the detection controller 68 may detect the air pressure inside the substrate carrier 22 without using the sensor 60. Instead, it may calculate the air pressure inside the substrate carrier 22 based on the flow rate of the exhaust gas 52 (detected by the gas flow rate sensor 64) and optionally the flow rate of the purge gas 50. The detection controller 68 may utilize other methods or mechanisms for detecting or measuring the air pressure inside the substrate carrier 22. Once knowing the value of the air pressure inside the substrate carrier 22, the detection controller 68 may then compare it with an expected or predefined air pressure range (i.e., having an upper limit and a lower limit). If the measured or detected air pressure value is outside the predefined air pressure range, then the health indicator is triggered to indicate that the substrate carrier 22 needs repair.

In an embodiment, the carrier purge station 14 generates the health indicator based on a measurement of humidity in the exhaust gas 52. For example, the detection controller 68 may read a humidity value of the exhaust gas 52 measured by the humidity sensor 62, and compare the measured humidity value with a predefined humidity range (i.e., having an upper limit and a lower limit). If the measured humidity value is outside the predefined humidity range, then the health indicator is triggered to indicate that the substrate carrier 22 needs repair.

In another embodiment, the carrier purge station 14 generates the health indicator based on a measurement of flow rate in the exhaust gas 52. For example, the detection controller 68 may read a flow rate value of the exhaust gas 52 measured by the gas flow rate sensor 64, and compare the measured flow rate value with a predefined flow rate range (i.e., having an upper limit and a lower limit). If the measured flow rate value is outside the predefined flow rate range, then the health indicator is triggered to indicate that the substrate carrier 22 needs repair. For example, a very low flow rate indicates that the air filter 32 and/or air filter 36 may have been clogged, and a very high flow rate indicates that the air filter 32 and/or air filter 36 may have been torn.

In yet another embodiment, the carrier purge station 14 generates the health indicator based on a measurement of particle sizes in the exhaust gas 52. For example, the detection controller 68 may read the maximum particle size detected by the particle sensor 66, and compare that value with a particle size threshold. If the detected particle size exceeds the particle size threshold, then the health indicator is triggered to indicate that the substrate carrier 22 needs repair. For example, having large particles in the exhaust gas 52 indicates that the air filter 36 has lost its expected filtration capability.

In yet another embodiment, the carrier purge station 14 generates the health indicator based on a measurement of particle count in the exhaust gas 52. For example, the detection controller 68 may read the particle count measured by the particle sensor 66, and compare that value with a particle count threshold. If the detected particle count exceeds the particle count threshold, then the health indicator is triggered to indicate that the substrate carrier 22 needs repair. For example, having too many particles in the exhaust gas 52 indicates that the air filter 32 and/or the air filter 36 have lost the expected filtration capability.

Figure 3:
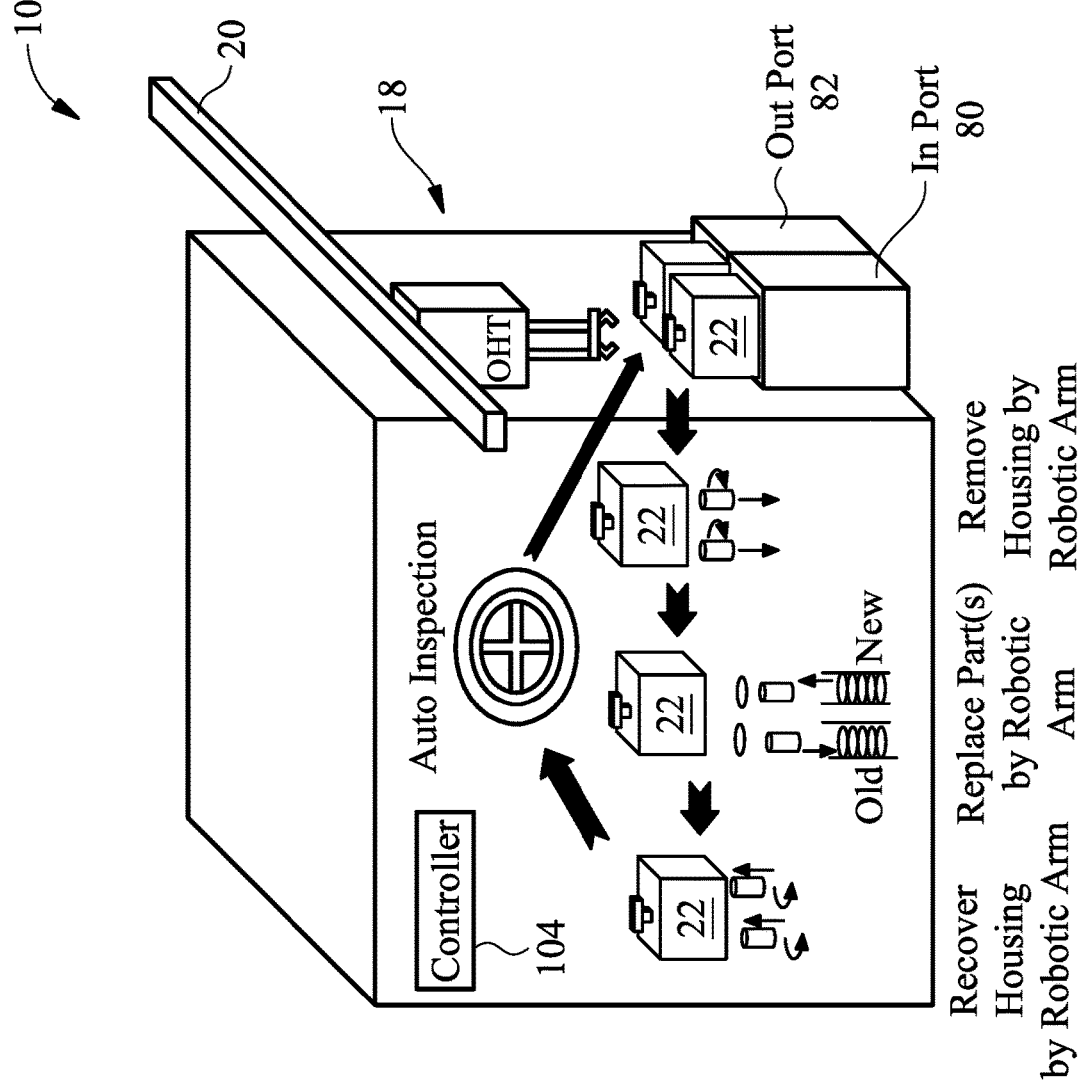
FIG. 3 illustrates a substrate carrier repair station and a workflow therein, according to various aspects of the present disclosure.

FIG. 3 illustrates an embodiment of the carrier repair station 18 and the OHT 20 in perspective view, and a workflow therein, according to various aspects of the present disclosure. Referring to FIG. 3, in the present embodiment, the carrier repair station 18 includes an input port 80 for receiving a substrate carrier 22 from the OHT 20 and an output port 82 for releasing the substrate carrier 22 to the OHT 20 after the repair. Between the input port 80 and the output port 82, the carrier repair station 18 further includes a first mechanism (e.g., a robotic arm) for removing screws, covers, and/or filter housing from the substrate carrier 22 to expose the air filters 32 and 36 (FIG. 2); and a second mechanism (e.g., one or more robotic arms) for removing the old air filters from and installing new air filters into the substrate carrier 22. In an embodiment, the carrier repair station 18 further includes a third mechanism (e.g., a robotic arm) for reinstalling the screws, covers, and/or filter housing into the substrate carrier 22. In an alternative embodiment, the first and third mechanisms share the same device or robotic arm(s). The carrier repair station 18 may further include an automatic inspection mechanism (e.g., optical sensors) for inspecting the newly installed air filters in the substrate carrier 22. The carrier repair station 18 includes a controller 104 for coordinating the workflow within the station.

Figure 4:
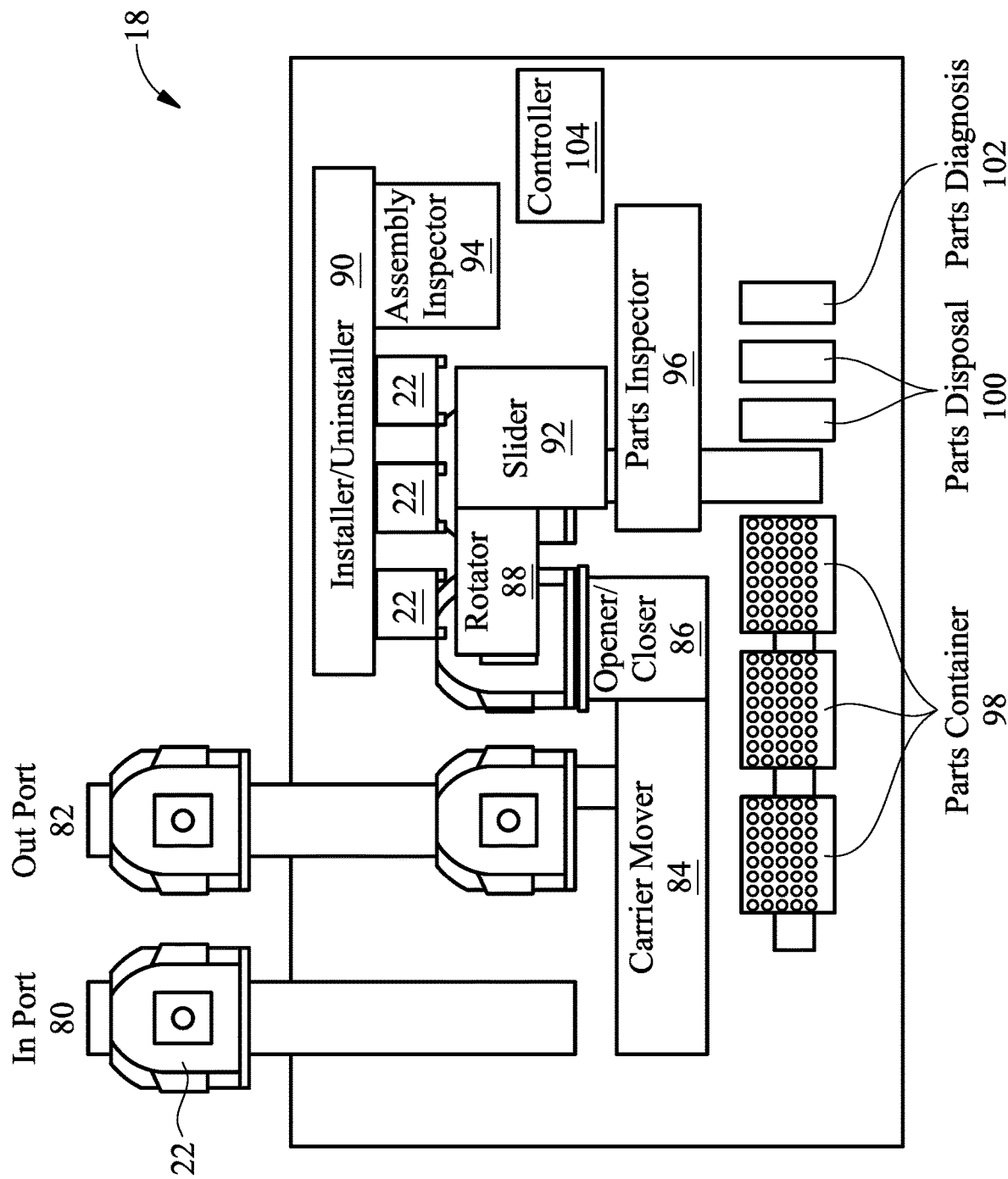
FIG. 4 illustrates a more detailed view of the substrate carrier repair station, in accordance with an embodiment.

FIG. 4 illustrates a more detailed view of the carrier repair station 18, in accordance with an embodiment. Referring to FIG. 4, the input port 80 and the output port 82 may be designed to hold one substrate carrier 22 at a time. Alternatively, they may be designed to hold multiple substrate carriers 22 at a time. Further, the input port 80 and the output port 82 may be designed to accommodate different types of substrate carriers 22, e.g., having different sizes and configurations. Once a substrate carrier 22 is received by the input port 80, a carrier mover 84 is operable to move the substrate carrier 22 from the input port 82 to other components of the carrier repair station 18 such as an opener/closer 86, a rotator 88, an installer/uninstaller 90, and an assembly inspector 94. FIG. 4 illustrates multiple substrate carriers 22 being repaired by the carrier repair station 18 in a streamlined fashion.

In the present embodiment, the rotator 88 is operable to rotate the substrate carrier 22 into a position so that the air filters and other parts of the substrate carrier 22 can be easily accessed by various components in the carrier repair station 18 such as the opener/closer 86, the installer/uninstaller 90, and the assembly inspector 94. For example, different types of substrate carriers (e.g., substrate carriers for FEOL, substrate carriers for BEOL, substrate carriers from different vendors, etc.) may have their air filters installed in different locations of the respective substrate carriers. The rotator 88 may be configured to rotate the substrate carriers 22 so that the air filters therein always appear in the same place with respect to the opener/closer 86, the installer/uninstaller 90, and the assembly inspector 94 regardless the type of the substrate carrier 22.

The opener/closer 86 is operable to open a filter housing of the substrate carrier 22, e.g., by unscrewing a cover and pulling out the filter housing, and to close the filter housing, e.g., by inserting the filter housing back into the substrate carrier and screwing the cover back on. The installer/uninstaller 90 is operable to remove old air filtration parts such as O-rings and air filters and install corresponding new parts. The assembly inspector 94 is operable to inspect newly installed parts, and particularly newly installed air filters. In an embodiment, the assembly inspector 94 includes a laser and/or optical sensors for detecting the flatness of the air filter after it has been installed into the substrate carrier 22. In another embodiment, the assembly inspector 94 includes a camera for taking an image of the air filter, which may be used by the controller 104 to determine the flatness of the air filter. In yet another embodiment, the assembly inspector 94 is operable to check the alignment of the newly installed air filter with respect to the inlet 30 and/or the outlet 34 (FIG. 2). After the substrate carrier 22 has passed the inspection by the assembly inspector 94, the carrier mover 84 may transfer the substrate carrier 22 to the output port 82.

The carrier repair station 18 further includes various components for supplying new parts such as new air filters and new O-rings to the installer/uninstaller 90. In the present embodiment, the carrier repair station 18 includes one or more parts containers 98 for holding the new parts, a parts inspector 96 for inspecting the new parts, a slider 92 for supplying the new parts that have passed the inspection to the installer/uninstaller 90, a parts disposal 100 for holding old parts that are removed from the substrate carrier 22, and a parts diagnosis container 102 for holding new parts that have failed the inspection. In an embodiment, the parts inspector 96 includes a camera (e.g., a CCD camera or a CMOS camera) for taking an image of a new part (e.g., a new air filter) and the controller 104 may determine from the image whether or not the new part has good quality, such as having expected size and shape and free of wrinkles and holes.

It is noted that the carrier repair station 18 in some embodiments may include additional components not shown herein and in some embodiments may omit some of the components discussed above. Further, some components discussed herein may be combined into one component in embodiments of the carrier repair station 18.

Figure 5:
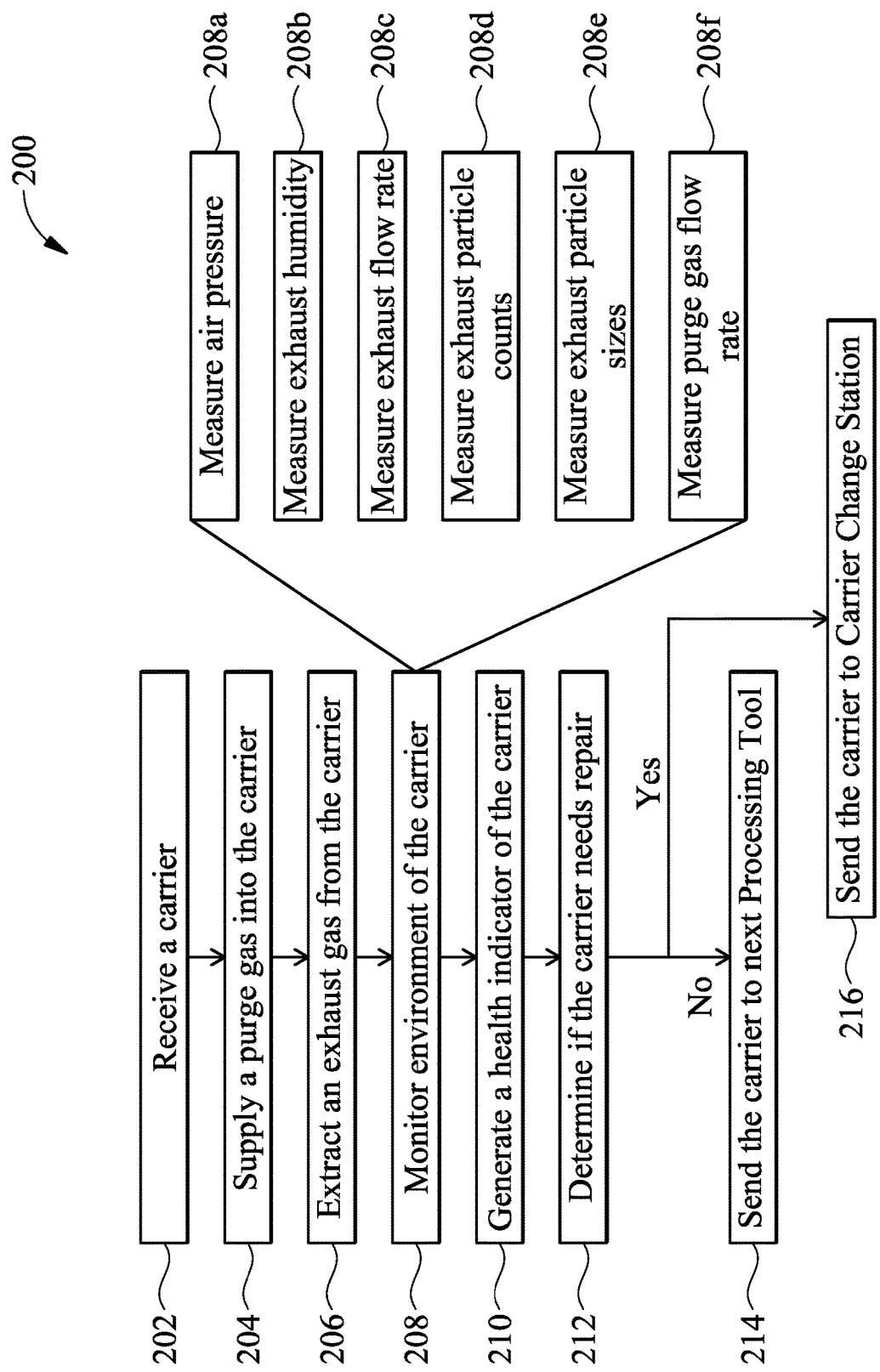
FIG. 5 shows a flow chart of a method for automatically detecting air filter deterioration in a substrate carrier, according to various aspects of the present disclosure.

FIG. 5 illustrates a flow chart of a method 200 for purging a substrate carrier and automatically detecting deterioration in the substrate carrier according to aspects of the present disclosure. For example, embodiments of the method 200 may be implemented by or with the carrier purge station 14. The method 200 is merely an example, and is not intended to limit the present disclosure beyond what is explicitly recited in the claims. Additional operations can be provided before, during, and after the method 200, and some operations described can be replaced, eliminated, or moved around for additional embodiments of the method. The method 200 is further described below in conjunction with FIGS. 1-2.

At operation 202, the method 200 (FIG. 5) receives a carrier, such as the substrate carrier 22. The carrier houses a plurality of substrates therein. With reference to FIG. 1, the carrier may be received by the carrier purge station 14 from one of the processing tools 12 or from the carrier change station 16 via the OHT 20. The plurality of substrates may be silicon wafers in one example. The carrier includes an inlet for receiving a purge gas and an outlet for discharging an exhaust gas. The carrier further includes an inlet air filter at the inlet and an outlet air filter at the outlet.

At operation 204, the method 200 (FIG. 5) supplies a purge gas into the carrier, e.g., through the inlet of the carrier. In some embodiments, the purge gas may be supplied at a flow rate of 1 to 15 liter per minute (L/min). The purge gas may include nitrogen gas, extra clean dry air, or other suitable inert gases. At operation 206, the method 200 extracts an exhaust gas from the carrier, e.g., through the outlet of the carrier. The operations 204 and 206 may be performed simultaneously. Further, the operations 204 and 206 may be performed for about 10 to 650 seconds in some embodiments.

While performing the operations 204 and 206, the method 200 (FIG. 5) further includes an operation 208 that monitors operational environment of the carrier. For example, the operation 208 may include one or more of the operations 208a, 208b, 208c, 208d, 208e, and 208f. The operation 208a measures air pressure inside the carrier. The operation 208b measures humidity in the exhaust gas. The operation 208c measures the flow rate of the exhaust gas. The operation 208d measures a particle count in the exhaust gas. The operation 208e measures particle sizes in the exhaust gas. The operation 208f measures the flow rate of the purge gas.

At operation 210, the method 200 (FIG. 5) generates a health indicator of the carrier based on the operational environment of the carrier. For example, the health indicator may be generated based on one or more of the following: (a)

whether the air pressure measured by the operation 208a is outside a predefined air pressure range, (b) whether the humidity level measured by the operation 208b is outside a predefined humidity range, (c) whether the exhaust flow rate measured by the operation 208c is outside a predefined flow rate range, (d) whether the particle count measured by the operation 208d exceeds a particle count threshold, and (e) whether the particle size measured by the operation 208e exceeds a particle size threshold. If one or more of the above conditions are satisfied, the health indicator takes a value indicating that the carrier is unhealthy. The method 200 may additionally or alternatively use other criteria to generate the health indicator.

At operation 212, the method 200 (FIG. 5) determines if the carrier needs repair. In an embodiment, if the health indicator indicates that the carrier is unhealthy, then the carrier is due for repair. In another embodiment, the method 200 may keep track of the number of purge operations applied to the same carrier. If that number exceeds a threshold, then the carrier is due for repair. For example, an air filter may have a maximum limit of use (i.e., the lifetime of the air filter), which may be specified by the air filter vendor or the carrier vendor. Once this limit is reached, the air filter has reached the end of its usable life and it is deemed unsafe for further uses. In this case, the method 200 may determine that the carrier needs repair regardless whether the health indicator indicates that the carrier is unhealthy.

If the operation 212 determines that the carrier does not need repair, the method 200 dispatches the carrier (operation 214) to the next processing tool for further fabrication processes. If the operation 212 determines that the carrier needs repair, the method 200 dispatches the carrier (operation 216) to a carrier change station where the substrates housed in the carrier may be removed from the carrier and placed into another carrier.

Figure 6:
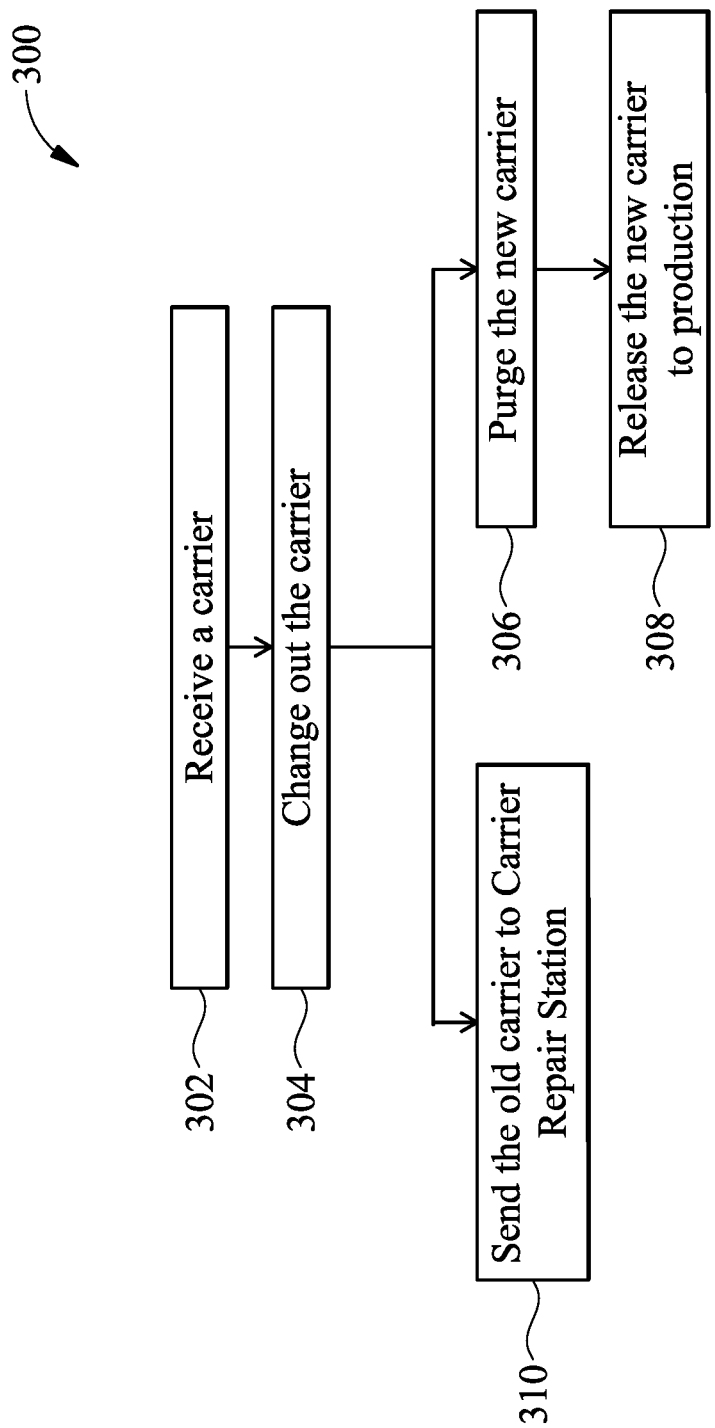
FIG. 6 shows a flow chart of a method for automatically replacing a substrate carrier, according to various aspects of the present disclosure.

FIG. 6 illustrates a flow chart of a method 300 for changing out a substrate carrier according to aspects of the present disclosure. For example, embodiments of the method 300 may be implemented by or with the carrier change station 16. The method 300 is merely an example, and is not intended to limit the present disclosure beyond what is explicitly recited in the claims. Additional operations can be provided before, during, and after the method 300, and some operations described can be replaced, eliminated, or moved around for additional embodiments of the method.

At operation 302, the method 300 receives a carrier with substrates housed therein. With reference to FIG. 1, the carrier may be received by the carrier change station 16 from the carrier purge station 14 via the OHT 20. At operation 304, the method 300 opens the carrier and moves the substrates from the carrier to another carrier ("new carrier"). At operation 306, the method 300 purges the new carrier with the substrates housed therein, for example, by the carrier purchase station 14 (FIG. 1). After purging, the method 300 releases the new carrier to production (operation 308), for example, by dispatching the new carrier with the substrates housed therein to a processing tool 12 (FIG. 1). At operation 310, the method 300 sends the old carrier to a carrier repair station, such as carrier repair station 18, for repair.

Figure 7:
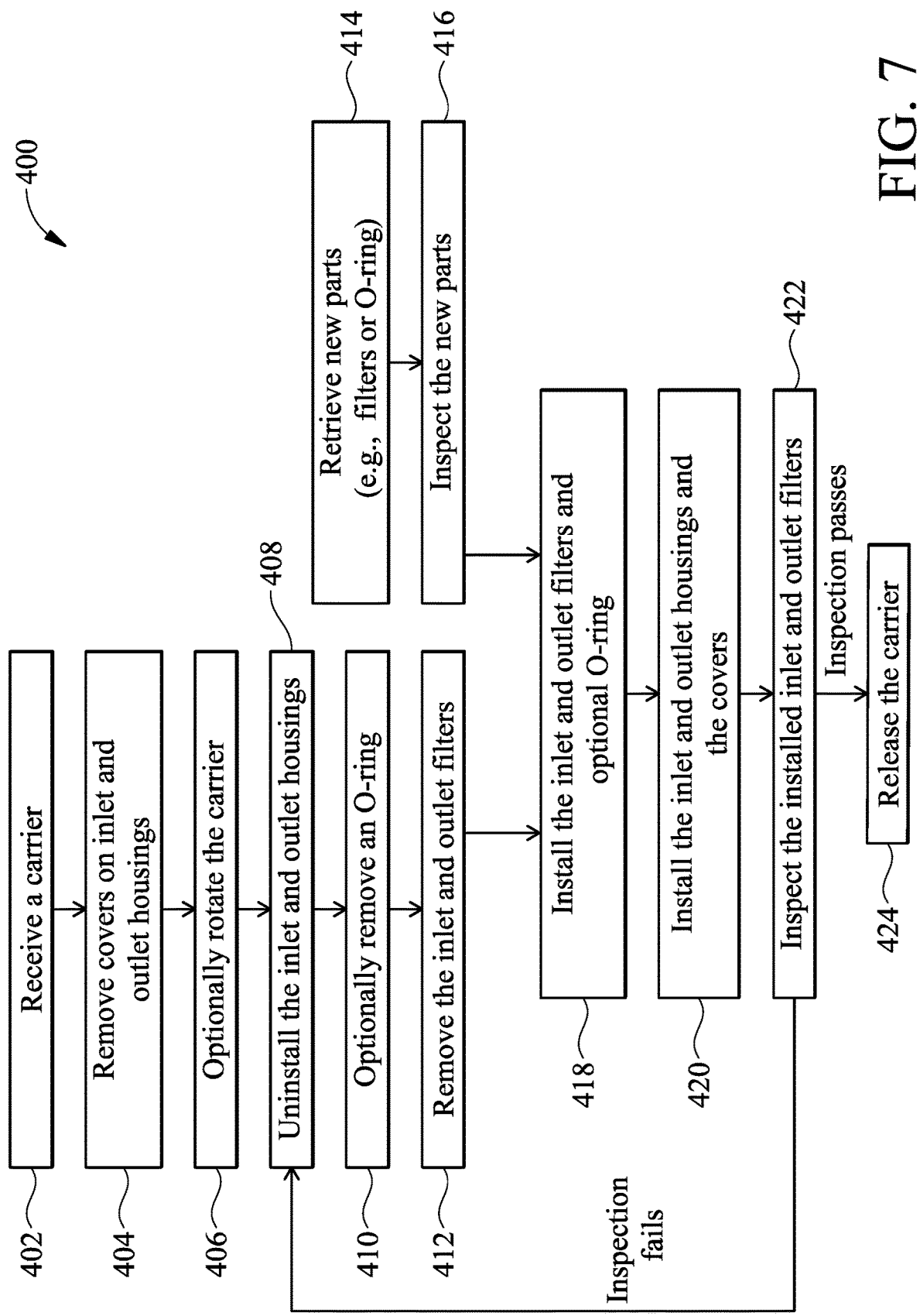
FIG. 7 shows a flow chart of a method for automatically replacing parts in a substrate carrier, according to various aspects of the present disclosure.

FIG. 7 illustrates a flow chart of a method 400 for repairing a substrate carrier according to aspects of the present disclosure. For example, embodiments of the method 400 may be implemented by or with the carrier repair station 18. The method 400 is merely an example, and is not intended to limit the present disclosure beyond what is explicitly recited in the claims. Additional operations can be provided before, during, and after the method 400, and some operations described can be replaced, eliminated, or moved around for additional embodiments of the method.

At operation 402, the method 400 (FIG. 7) receives a carrier. In the present embodiment, the carrier is free of substrates therein. With reference to FIG. 1, the carrier may be received by the carrier repair station 18 from the carrier change station 16 via the OHT 20. Particularly, the carrier may be received by the input port 80 of the carrier repair station 18 (FIGS. 3-4).

At operation 404, the method 400 (FIG. 7) removes covers on inlet and outlet housings of the carrier, for example, by unscrewing the covers. At operation 406, the method 400 optionally rotates the carrier so that the housing and air filters therein may be easily accessed. An operation 408, the method 400 uninstalls the inlet and outlet housings from the carrier to expose the air filters in the carrier. At operation 410, the method 400 removes an O-ring, if any, from the carrier. At operation 412, the method 400 removes inlet and outlet air filters from the carrier.

At operation 414, the method 400 (FIG. 7) retrieves new parts to be installed into the carrier, such as new air filters and optionally new O-rings. At operation 416, the method 400 inspects the new parts to ensure that they are free of defects. If the defects are found in the new parts, the method 400 may repeat the operations 414 and 416 until it finds new parts free of defects.

At operation 418, the method 400 (FIG. 7) installs the new parts, such as new inlet and outlet air filters, into the carrier. The method 400 may optionally install new O-rings into the carrier if needed. At operation 420, the method 400 reinstalls the inlet and outlet housings and the covers back onto the carrier. At operation 422, the method 400 inspects the newly installed parts. For example, it may use optical sensors to detect surface flatness of newly installed air filters. If the newly installed parts fail the inspection, the method 400 goes back to the operation 408 and repeats the operations 408-422. If the newly installed parts pass the inspection, the method 400 releases the carrier back to production (operation 424). With reference to FIGS. 3-4, the carrier may be placed into the output report 82 and waits for dispatching via the OHT 20.

In an embodiment, one or more of the above operations of the method 400 are implemented with computerized mechanical devices, such as robotic arms. This advantageously reduces fabrication downtime and increases the reliability and quality of the carrier.

Although not intended to be limiting, one or more embodiments of the present disclosure provide many benefits to semiconductor fabrication. For example, embodiments of the present disclosure automatically detect deterioration in a substrate carrier, which reduces manual work and increases production efficiency. It is also more reliable and timely, thereby reducing wafer defects. Further, embodiments of the present disclosure automatically replace deteriorated air filters in substrate carriers, thereby increasing production efficiency and reducing operational errors.

In one exemplary aspect, the present disclosure is directed to a method. The method includes receiving a carrier with a plurality of wafers inside; supplying a purge gas to an inlet of the carrier; extracting an exhaust gas from an outlet of the carrier; and generating a health indicator of the carrier while performing the supplying of the purge gas and the extracting of the exhaust gas.

In an embodiment of the method, the generating of the health indicator is based on one or more of following: (a) a measurement of air pressure inside the carrier, (b) a measurement of humidity of the exhaust gas, (c) a measurement of a flow rate of the exhaust gas, and (d) a measurement of particles in the exhaust gas.

In another embodiment of the method, the generating of the health indicator includes reading an air pressure value measured by a pressure sensor installed inside the carrier; comparing the air pressure value with a predefined air pressure range; and indicating that the carrier needs repair when the air pressure value is outside the predefined air pressure range.

In another embodiment of the method, the generating of the health indicator includes reading a humidity value of the exhaust gas measured by a humidity sensor installed adjacent the outlet of the carrier; comparing the humidity value with a predefined humidity range; and indicating that the carrier needs repair when the humidity value is outside the predefined humidity range.

In another embodiment of the method, the generating of the health indicator includes measuring a flow rate of the exhaust gas; comparing the flow rate with an predefined flow rate range; and indicating that the carrier needs repair when the flow rate is outside the predefined flow rate range.

In another embodiment of the method, the generating of the health indicator includes measuring sizes of particles carried in the exhaust gas; comparing the sizes with a size threshold; and indicating that the carrier needs repair when one of the sizes exceeds the size threshold.

In yet another embodiment of the method, the generating of the health indicator includes measuring a count of particles carried in the exhaust gas; comparing the count with a count threshold; and indicating that the carrier needs repair when the count exceeds the count threshold.

In an embodiment, when the health indicator indicates that the carrier needs repair, the method further includes removing the plurality of wafers from the carrier; and dispatching the carrier to a carrier repair station through an overhead transport (OHT). In a further embodiment, the method includes receiving the carrier by the carrier repair station; replacing, by a first motorized tool, an inlet filter at the inlet of the carrier with a new inlet filter; replacing, by a second motorized tool, an outlet filter at the outlet of the carrier with a new outlet filter; and inspecting, by a third motorized tool, the new inlet filter and the new outlet filter. In a further embodiment, the method includes, on condition that both the new inlet filter and the new outlet filter pass the inspection, dispatching the carrier with the new inlet filter and the new outlet filter to a process tool through the OHT. In another for the embodiment, the method includes, on condition that one of the new inlet filter and the new outlet filter fails the inspection, replacing the one of the new inlet filter and the new outlet filter with a replacement filter; and inspecting the replacement filter.

In another exemplary aspect, the present disclosure is directed to an apparatus for semiconductor manufacturing. The apparatus includes an input port to receive a carrier, wherein the carrier includes a carrier body, a housing installed onto the carrier body, and a filter installed between the carrier body and the housing; a first robotic arm to uninstall the housing from the carrier and to install the housing into the carrier; one or more second robotic arms to remove the filter from the carrier and to install a new filter into the carrier; and an output port to release the carrier to production.

In an embodiment, the one or more second robotic arms are further configured to install and uninstall an O-ring between the filter and the housing. In an embodiment, the apparatus further includes a first inspection mechanism to inspect the new filter before it is installed by the one or more second robotic arms. In an embodiment, the first inspection mechanism includes a camera to take an image of the new filter; and a controller to determine quality of the new filter based on the image.

In an embodiment, the apparatus further includes a second inspection mechanism to inspect the new filter after it has been installed by the one or more second robotic arms. In an embodiment, the second inspection mechanism includes a laser mechanism to detect flatness of a surface of the new filter.

In another exemplary aspect, the present disclosure is directed to a system. The system includes a plurality of semiconductor processing tools; a carrier purge station; a carrier repair station; and an overhead transport (OHT) loop for transporting one or more substrate carriers among the plurality of semiconductor processing tools, the carrier purge station, and the carrier repair station. The carrier purge station is configured to receive a substrate carrier from one of the plurality of semiconductor processing tools, purge the substrate carrier with an inert gas, and determine if the substrate carrier needs repair. The carrier repair station is configured to receive a substrate carrier to be repaired and replace one or more parts in the substrate carrier.

In an embodiment, the system further a carrier change station configured to receive a substrate carrier with substrates, remove the substrates from the substrate carrier, and place the substrates into another substrate carrier.

In another embodiment of the system, the carrier purge station is configured to determine if the substrate carrier needs repair based on at least one of following: whether the one or more parts in the substrate carrier have reached their respective lifetime; a measurement of air pressure inside the substrate carrier while purging the substrate carrier; a measurement of exhaust humidity while purging the substrate carrier; a measurement of an exhaust flow rate while purging the substrate carrier; and a measurement of particles in exhaust while purging the substrate carrier.

In an embodiment of the system, the one or more parts include an air filter in the substrate carrier. In another embodiment of the system, the substrate carrier is configured to carry a plurality of wafers.

In another exemplary aspect, the present disclosure is directed to a method. The method includes purging a wafer carrier to produce an exhaust gas; and determining if the wafer carrier needs repair based on one or more of following: whether air pressure inside the wafer carrier is within a predefined air pressure range, whether humidity of the exhaust gas is within a predefined humidity range, whether a flow rate of the exhaust gas is within a predefined flow rate range, whether sizes of particles in the exhaust gas are smaller than a size threshold, whether a count of particles in the exhaust gas is smaller than a count threshold, and whether a filter in the wafer carrier has reached its end of life.

In an embodiment, when the determining determines that the wafer carrier needs repair, the method further includes sending the wafer carrier to a carrier repair station using an overhead transport (OHT) loop; and replacing one or more parts of the wafer carrier by the carrier repair station. In a further embodiment, the replacing of the one or more parts includes: receiving the wafer carrier using the OHT loop; removing the one or more parts from the wafer carrier with at least one robotic arm; installing one or more replacement parts into the wafer carrier with at least another robotic arm; and inspecting the one or more replacement parts with at least one optical device. In a further embodiment, on condition that the one or more replacement parts pass the inspection, the method further includes releasing the wafer carrier to a semiconductor processing tool using the OHT loop.

In another exemplary aspect, the present disclosure is directed to an apparatus. The apparatus includes an input port to receive a wafer carrier; a supply container to hold a plurality of new air filters; a first mechanism to remove an air filter from the wafer carrier; a second mechanism to pick up a new air filter from the supply container; a third mechanism to install the new air filter into the wafer carrier; and an output port to deliver the wafer carrier after the new air filter has been installed.

In an embodiment, the apparatus further includes a rotator to rotate the wafer carrier. In another embodiment, the apparatus further includes a fourth mechanism to remove a housing from the wafer carrier to expose the air filter, wherein the fourth mechanism is configured to re-install the housing after the new air filter has been installed.

In an embodiment, the apparatus further includes a first inspection mechanism to inspect the new air filter before it is installed into the wafer carrier. In an embodiment, the apparatus further includes a disposal container to receive the air filter after it is removed from the wafer carrier. In yet another embodiment, the apparatus further includes a second inspection mechanism to inspect the new air filter after it is installed into the wafer carrier.

In yet another exemplary aspect, the present disclosure is directed to a system. The system includes a plurality of semiconductor processing tools; a wafer carrier; a wafer carrier purge station; a wafer carrier change station; a wafer carrier repair station; and an overhead transport (OHT) system for transporting the wafer carrier among the semiconductor processing tool, the wafer carrier purge station, the wafer carrier change station, and the wafer carrier repair station.

In an embodiment of the system, one of the plurality of semiconductor processing tools is configured to: receive the wafer carrier with a plurality of wafers using the OHT system; process the plurality of wafers, resulting in a plurality of processed wafers; and transfer the plurality of processed wafers to the wafer carrier to be sent to the wafer carrier purge station using the OHT system.

In another embodiment, the wafer carrier purge station is configured to: receive the wafer carrier with a plurality of wafers using the OHT system; supply a purge gas into the wafer carrier; and monitor an exhaust gas from the wafer carrier. In a further embodiment, the wafer carrier purge station is configured to monitor the exhaust gas to determine at least one of: humidity of the exhaust gas; a flow rate of the exhaust gas; a particle count in the exhaust gas; and particle sizes in the exhaust gas. In another further embodiment, the wafer carrier purge station is further configured to monitor air pressure inside the wafer carrier. In yet another further embodiment, the wafer carrier purge station is further configured to determine whether the wafer carrier needs repair.

In an embodiment of the system, the wafer carrier change station is configured to: receive the wafer carrier with a plurality of wafers using the OHT system; move the plurality of wafers from the wafer carrier into another wafer carrier; and send the wafer carrier without any wafer to the wafer carrier repair station using the OHT system. In a further embodiment, the wafer carrier repair station is configured to: receive the wafer carrier without any wafer using the OHT system; remove a housing from the wafer carrier to expose an air filter; replace the air filter with a new air filter; re-install the housing into the wafer carrier; and release the wafer carrier with the new air filter using the OHT system.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. An apparatus for semiconductor manufacturing, comprising:
   an input port to receive a carrier, wherein the carrier includes a carrier body, a housing installed onto the carrier body, and a filter installed between the carrier body and the housing;
   a first robotic arm configured to uninstall the housing from the carrier and to reinstall the housing into the carrier;
   one or more second robotic arms configured to remove the filter from the carrier and to install a new filter into the carrier; and
   an output port to release the carrier to production.

2. The apparatus of claim 1, wherein the one or more second robotic arms are further configured to install and uninstall an O-ring between the filter and the housing.

3. The apparatus of claim 1, further comprising:
   a first inspection mechanism configured to inspect the new filter before it is installed by the one or more second robotic arms.

4. The apparatus of claim 3, wherein the first inspection mechanism includes:
   a camera to take an image of the new filter; and
   a controller configured to determine quality of the new filter based on the image.

5. The apparatus of claim 1, further comprising:
   a second inspection mechanism configured to inspect the new filter after it has been installed by the one or more second robotic arms.

6. The apparatus of claim 5, wherein the second inspection mechanism includes a laser mechanism to detect flatness of a surface of the new filter.

7. The apparatus of claim 1, further comprising:
   a rotator for rotating the carrier before the carrier is accessed by the first robotic arm.

8. The apparatus of claim 1, further comprising:
   a supply container for holding new parts including new filters.

9. The apparatus of claim 1, further comprising:
   a parts disposal for holding parts removed from the carrier.

10. An apparatus for semiconductor manufacturing, comprising:
    an input port to receive a substrate carrier, wherein the substrate carrier includes a carrier body, a housing, and an air filter installed between the carrier body and the housing;
    a first robotic arm configured to uninstall the housing from the substrate carrier;
    one or more second robotic arms configured to remove the air filter from the substrate carrier;

a controller configured to determine quality of a new air filter before the new air filter is installed into the substrate carrier; and an output port to release the substrate carrier to production after the new air filter is installed.

11. The apparatus of claim 10, further comprising:
a camera to take an image of the new air filter, wherein the controller is configured to determine the quality of the new air filter based on the image.

12. The apparatus of claim 10, further comprising:
an inspector configured to inspect the new air filter after the new air filter has been installed into the substrate carrier.

13. The apparatus of claim 12, wherein the inspector is configured to use a laser to detect flatness of a surface of the new air filter.

14. The apparatus of claim 10, further comprising:
a supply container for holding new parts including new air filters; and
a parts disposal for holding parts removed from the substrate carrier.

15. The apparatus of claim 10, wherein the input port and the output port are configured to be attached to an overhead transport (OHT).

16. The apparatus of claim 10, wherein the one or more second robotic arms are further configured to install the new air filter into the substrate carrier, and the first robotic arm is further configured to reinstall the housing into the substrate carrier after the new air filter has been installed into the substrate carrier.

17. An apparatus for semiconductor manufacturing, comprising:
an input port to receive a substrate carrier, wherein the substrate carrier includes a carrier body, a housing, and a filter installed between the carrier body and the housing;
a first mechanism configured to uninstall the housing from the substrate carrier;
a second mechanism configured to remove the filter from the substrate carrier;
a controller configured to determine quality of a new filter;
a third mechanism configured to inspect the new filter after the new filter is installed into the substrate carrier; and
an output port to release the substrate carrier to production after the new filter is installed into the substrate carrier and is inspected.

18. The apparatus of claim 17, wherein the first mechanism is further configured to reinstall the housing into the substrate carrier after the new filter has been installed into the substrate carrier.

19. The apparatus of claim 17, wherein the second mechanism is further configured to install the new filter into the substrate carrier.

20. The apparatus of claim 17, wherein the controller is configured to determine the quality of the new filter based on an image of the new filter.

* * * * *